(12) United States Patent
Scheuber et al.

(10) Patent No.: US 10,843,325 B2
(45) Date of Patent: Nov. 24, 2020

(54) QUICK COUPLING APPARATUS ON INSTRUMENT HANDLE

(71) Applicant: Depuy Synthes Products, Inc., Raynham, MA (US)

(72) Inventors: Patricia Scheuber, Zuchwil (CH); This Aebi, Grenchen (CH); Rhett A. Rapier, Trimbach (CH); Felix Vellappallil, Suhr (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 591 days.

(21) Appl. No.: 15/453,664

(22) Filed: Mar. 8, 2017

(65) Prior Publication Data
US 2018/0257214 A1  Sep. 13, 2018

(51) Int. Cl.
| | |
|---|---|
| *B25G 3/04* | (2006.01) |
| *B25G 3/18* | (2006.01) |
| *F16B 21/09* | (2006.01) |
| *A61B 17/16* | (2006.01) |
| *A61B 17/92* | (2006.01) |
| *A61B 17/00* | (2006.01) |

(52) U.S. Cl.
CPC .............. *B25G 3/04* (2013.01); *A61B 17/162* (2013.01); *B25G 3/18* (2013.01); *A61B 17/1604* (2013.01); *A61B 17/1659* (2013.01); *A61B 17/92* (2013.01); *A61B 2017/0046* (2013.01); *F16B 21/09* (2013.01)

(58) Field of Classification Search
CPC ... B25G 3/04; B25G 3/08; B25G 3/12; B25G 3/18; B25G 3/26; Y10T 403/59; Y10T 403/591; Y10T 403/598; Y10T 403/599; Y10T 403/60; Y10T 403/602; F16B 7/042; F16B 7/0426; F16B 21/09; F16B 21/16; B25B 23/0007; B25B 23/0035; B25B 23/0042; B25D 2250/111
See application file for complete search history.

(56) References Cited

U.S. PATENT DOCUMENTS

| | | | | |
|---|---|---|---|---|
| 3,474,506 A | * | 10/1969 | Metz | F16B 19/109 |
| | | | | 411/347 |
| 3,740,100 A | * | 6/1973 | Perego | B60B 37/10 |
| | | | | 301/121 |

(Continued)

FOREIGN PATENT DOCUMENTS

| | | | | |
|---|---|---|---|---|
| DE | 102006032970 A1 | * | 1/2008 | ......... B25B 23/0035 |
| EP | 1302168 A1 | | 4/2003 | |

(Continued)

OTHER PUBLICATIONS

Written Opinion of the International Searching Authority for PCT/US2018/021034 dated Oct. 11, 2018.

(Continued)

*Primary Examiner* — Jonathan P Masinick
(74) *Attorney, Agent, or Firm* — Kramer Amado, P.C.

(57) ABSTRACT

Disclosed is an apparatus for use with an instrument handle, the apparatus including a housing, a knob receivable in the housing, the knob having a key hole structure to receive an instrument bulb and neck, a slot in the housing to receive the knob, wherein the knob is pressed into the slot to facilitate installation and removal of the instrument bulb and neck.

21 Claims, 6 Drawing Sheets

(56) References Cited

U.S. PATENT DOCUMENTS

| | | | |
|---|---|---|---|
| 5,352,235 A | 10/1994 | Koros et al. | |
| 5,975,592 A * | 11/1999 | Lin | B25G 3/18 |
| | | | 292/159 |
| 6,139,214 A | 10/2000 | Zirps et al. | |
| 7,587,791 B2 * | 9/2009 | Liou | B25B 23/0035 |
| | | | 16/422 |
| 7,618,211 B2 * | 11/2009 | Wood | E21B 17/046 |
| | | | 403/327 |
| 8,500,358 B1 * | 8/2013 | Cassidy | A63B 21/156 |
| | | | 403/322.2 |
| 8,800,113 B1 * | 8/2014 | Charvet | B25G 3/18 |
| | | | 16/422 |
| 9,255,591 B2 * | 2/2016 | Carnevali | F16D 1/116 |
| 10,047,779 B2 * | 8/2018 | Wang | F16B 21/09 |
| 2010/0054852 A1 * | 3/2010 | Snyder | B25G 1/04 |
| | | | 403/301 |
| 2014/0052187 A1 | 2/2014 | McBride et al. | |

FOREIGN PATENT DOCUMENTS

| | | |
|---|---|---|
| WO | 2007/008087 A1 | 1/2007 |
| WO | 2013112308 A1 | 8/2013 |
| WO | 2014/091454 A1 | 6/2014 |

OTHER PUBLICATIONS

Notification of Transmittal of the International Search Report and the Written Opinion of the International Searching Authority, or the Declaration for PCT/US2018/021034 dated Oct. 11, 2018.

* cited by examiner

QUICK COUPLING APPARATUS ON INSTRUMENT HANDLE

TECHNICAL FIELD

Embodiments described herein include a coupling apparatus to hold and release a variety of interchangeable instruments.

BACKGROUND

Coupling apparatuses that couple instruments to handles may have problems such as bending and breaking of internal components such as a pin, or an instrument getting stuck in a coupling. Some problems may occur when a hammer hits a handle when there is no resistance on a front of an instrument. Inertia and the design of parts may allow the parts to move in an unwanted decoupling direction. Also, a small coupling area can lead to permanent deformation in the contact area.

SUMMARY

A brief summary of various embodiments is presented below. Some simplifications and omissions may be made in the following summary, which is intended to highlight and introduce some aspects of the various embodiments, but not to limit the scope of the invention. Detailed descriptions of embodiments adequate to allow those of ordinary skill in the art to make and use the inventive concepts will follow in later sections.

Various exemplary embodiments are related to an apparatus for use with an instrument handle, the apparatus including a housing, a knob receivable in the housing, the knob having a key hole structure to receive an instrument bulb and neck, a slot in the housing to receive the knob, wherein the knob is pressed into the slot to facilitate installation and removal of an instrument.

The apparatus may further include at least one spring, and at least one spring support attached to the knob configured to compress and release the at least one spring.

The release of the at least one spring may place the knob into locked position.

The compression of the at least one spring may place the knob into open position to facilitate installation and removal of the instrument.

The slot may be cylindrical.

The knob may have the shape of a rectangular cuboid.

The knob may have rounded edges to fit within the cylindrical slot.

The knob may include a milling groove to prevent unwanted decoupling of an inserted instrument.

The housing may have a height and the knob may be pressed into the slot below the height in order to install or remove the instrument.

The housing may be configured to receive a replaceable instrument having a bulb, neck, and shaft.

The key hole structure may include an instrument receiving portion, and an angled coupling surface to couple with an instrument.

The coupling surface may have a circular shape configured to receive a neck of the instrument on greater than one hundred eighty degrees of a circumference thereof.

The apparatus may include a plurality of drain holes formed in the housing.

The plurality of drain holes may be formed on a side of the housing opposite to a mounting direction of the knob in the housing.

The knob may include a pressing spot having a concave surface.

The housing may include a pin hole configured to receive a pin in a direction perpendicular to a mounting direction of the knob in the housing.

The housing may include overhanging portions to prevent the instrument from rotating when coupled to the apparatus.

Various exemplary embodiments are also related to a method of using a housing having a height and a knob inserted therein to lock an instrument into place, including pressing the knob below the height of the housing to allow removal and installation of an instrument tip, and releasing the knob to lock the instrument tip into place.

The instrument tip may be received into a key hole structure of the housing, the key hole structure having an instrument receiving portion, a coupling surface, and a milling groove.

The method may include shifting the knob from a first position to a second position to lock an instrument into place, wherein in the first position a neck of an instrument is substantially within the instrument receiving portion and in the second position the neck of the instrument is substantially within the coupling surface.

BRIEF DESCRIPTION OF THE DRAWINGS

Additional objects and features of the invention will be more readily apparent from the following detailed description and appended claims when taken in conjunction with the drawings. Although several embodiments are illustrated and described, like reference numerals identify like parts in each of the figures, in which:

DETAILED DESCRIPTION

It should be understood that the figures are merely schematic and are not drawn to scale. It should also be understood that the same reference numerals are used throughout the figures to indicate the same or similar parts.

The descriptions and drawings illustrate the principles of various example embodiments. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments. As used herein, the terms "context" and "context object" will be understood to be synonymous, unless otherwise indicated. Descriptors such as "first," "second," "third," etc., are not meant to limit the order of elements discussed, are used to distinguish one element from the next, and are generally interchangeable.

Numbering of components is generally performed with newly introduced parts initiating a new reference numeral being used. In some drawings, to prevent over-numbering, component parts from previous drawing figures are carried over into later drawing figures.

Figures 1, 2, 3:
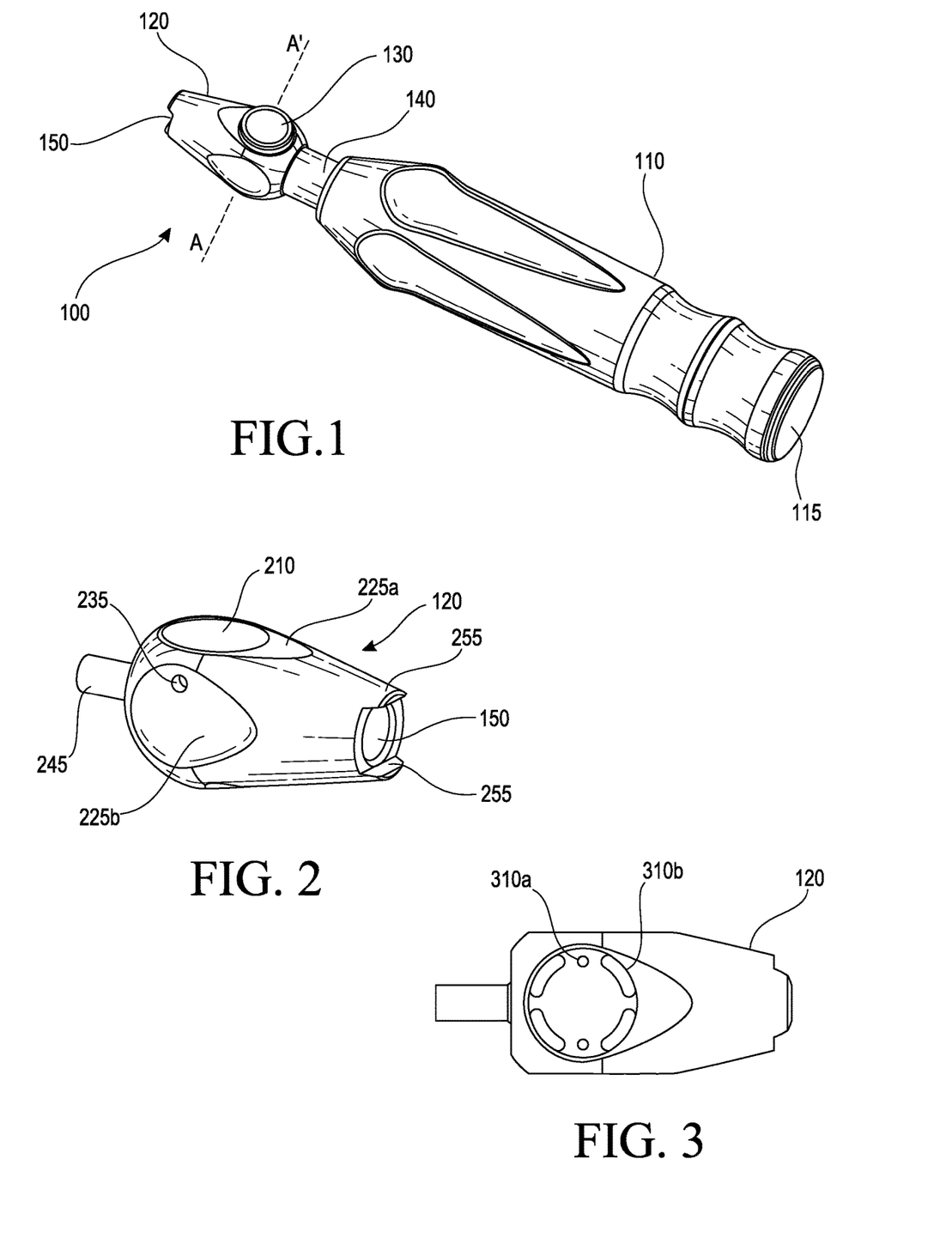
FIG. 1 illustrates a perspective view of a quick coupling apparatus on an instrument handle in accordance with embodiments described herein.
FIG. 2 illustrates a perspective view of a housing of the quick coupling apparatus in accordance with embodiments described herein.
FIG. 3 illustrates a bottom view of the housing in accordance with FIG. 2.

FIG. 1 illustrates a perspective view of a quick coupling apparatus 100 on an instrument handle 110 in accordance with embodiments described herein. The quick coupling apparatus 100 includes a housing 120 into which a knob 130 has been inserted and coupled. The instrument handle 110 may have a proximal end adjacent the quick coupling apparatus 100 and a distal end at a far end from the quick coupling apparatus 100. A hammer or other striking instrument (not illustrated) may be applied against a strike cap 115 at the distal end of the instrument handle 110 to drive an instrument coupled to the quick coupling apparatus 100 in a direction of the strike. The handle 110 may include a main portion 140 that is overmolded with a silicone covering or the like for gripping purposes. The main portion 140 may extend through the covering and be connected to the housing 120 of the quick coupling apparatus 100 by a weld or other method. The housing 120 may be a casted metal piece made of aluminum or similar metal or alloy. The housing 120 may include an instrument opening 150 configured to receive and release any one of a plurality of interchangeable instruments including chisels, files, knives, mallots, bone curettes, elevators, or the like. As illustrated in FIG. 1, the knob 130 protrudes from the housing 120 in a locked position.

FIG. 2 illustrates a perspective view of the housing 120 of the quick coupling apparatus 100 in accordance with embodiments described herein. The housing 120 includes a connecting rod 245. The connecting rod 245 is inserted into the main portion 140 of the handle 110 which is then welded to the housing 120. The shape or cross-section of the housing 120 is larger towards the connecting rod 245 and tapers to become narrower closer to the instrument opening 150. The wider portion of the housing 120 is configured to receive the knob 130 of sufficient size to couple inserted instruments to the housing 120. The narrower portion of the housing 120 includes overhanging portions 255. The overhanging portions 255 are rounded on external sides thereof and flat on internal sides. The internal flat sides of the overhanging portions 255 couple with flat sections of an instrument to prevent the instrument from rotating when coupled to the quick coupling apparatus 100.

External features of the housing 120 include several teardrop or waterdrop surface shapes 225a and 225b through which several apparatus elements are received. Through the first waterdrop shape 225a is manufactured a slot 210 to receive the knob 130 as described herein. Through the second waterdrop shape 225b is a pin hole 235 positioned on one side thereof. As described in embodiments herein, after the knob 130 has been inserted into the slot 210, a pin will be inserted into the pin hole 235 to prevent the knob 130 from being removed from the housing 120, thus capturing the knob 130 in the slot 210 and being able to couple an instrument to the quick coupling apparatus 100.

FIG. 3 illustrates a bottom view of the housing 120 in accordance with FIG. 2. Embodiments described herein provide for ease in cleaning the quick coupling apparatus 100 without having to remove an inserted knob 130 from the housing 120 or removing the quick coupling apparatus 100 from the handle 110. On one side of the housing 120 are manufactured a plurality of drain holes 310a and 310b. The drain holes may be designed and manufactured to have various shapes such as circles 310a or elongated ovals 310b, but are not limited thereto and may take on various shapes to achieve the given purpose. The drain holes 310b may be curved to correspond to a cylindrically shaped slot that is formed in the housing 120. The drain holes 310a may correspond to springs that will be described below. The drain holes and other gaps between the knob 130 and the housing 120 also permit the quick coupling apparatus 100 to stay fastened to the instrument handle 110 for cleaning or reprocessing.

Figure 4:
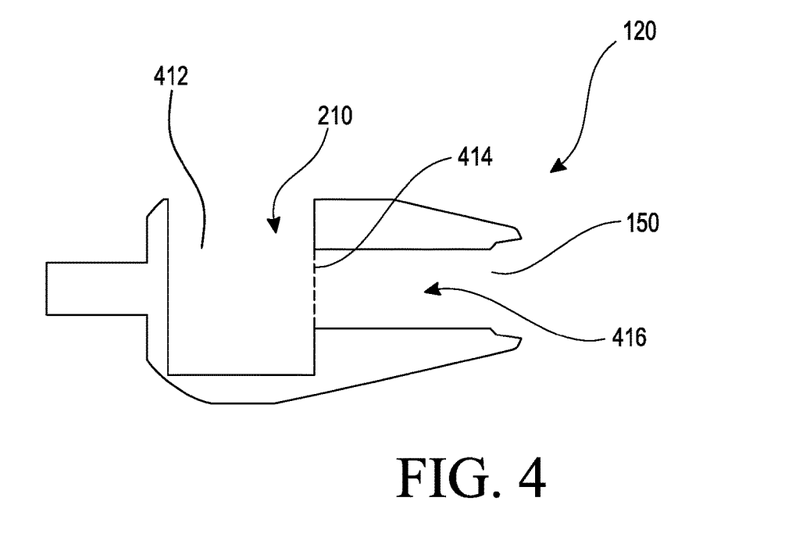
FIG. 4 illustrates a cross-sectional view of the housing in accordance with FIG. 2.

FIG. 4 illustrates a cross-sectional view of the housing 120 in accordance with FIG. 2. The housing 120 includes the slot 210 extending into the housing 120 in a first direction into which a knob 130 is inserted. The slot 210 may have a cylindrical shape. The slot 210 extends into but not completely through the housing 120. The slot 210 includes a first slot opening 412 into which the knob 130 is inserted. The slot 210 includes a second slot opening 414 through which a received instrument bulb, neck, and shaft of a replaceable instrument will be received to couple to the knob 130. At one end of the housing 120 is the instrument opening 150 in which the instrument is initially mounted. The instrument will pass through and be secured within a channel 416 disposed between the second slot opening 414 and the instrument opening 150. The slot 210 may extend in a first direction that is the direction in which the knob 130 is received in the slot 210. The channel 416 may extend in a second direction substantially perpendicular to the first direction to receive the instrument.

Figure 5:
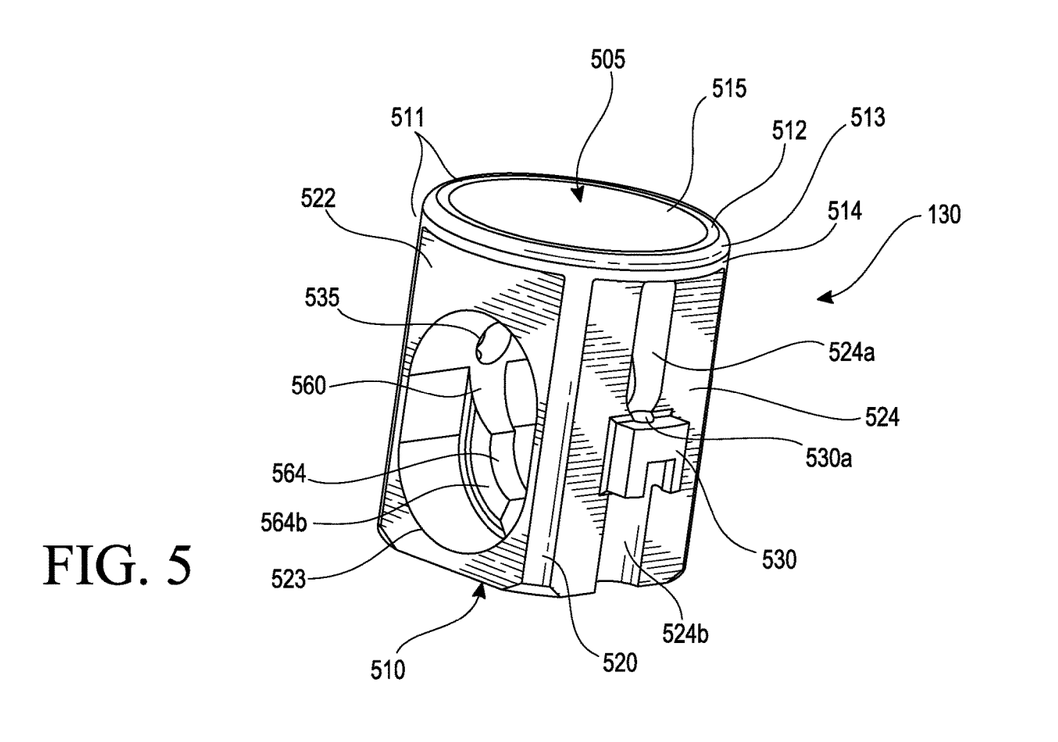
FIG. 5 illustrates a perspective view of the knob in accordance with embodiments described herein.

FIG. 5 illustrates a perspective view of the knob 130 in accordance with embodiments described herein. The knob 130 may generally have a shape of a rectangular cuboid with four walls. The knob 130 may include an upper portion 505 adjacent the four walls and a flat lower surface 510 opposite the upper portion 505. The upper portion 505 of the knob 130 may be round, rectangular, or other shape to facilitate pressing the knob 130 into the slot 210. The knob 130 may be a casted metal piece made of aluminum or similar metal or alloy. The rectangular cuboid shape of the knob 130 provides space between the four walls and the cylindrical slot 210 in order for water, liquids, debris, and small particles to pass through the quick coupling apparatus 100 for ease of cleaning. The upper portion 505 of the knob 130 may include an indented concave pressing spot 515 that a user may press to facilitate coupling, uncoupling, and removal of an instrument to the quick coupling apparatus 100.

Because the slot 210 has a circular cylindrical shape, the knob 130 may include four rounded corner portions 520 respectively connecting the four walls to allow the knob 130 to fit and slide within the slot 210. The rounded corner portions 520 enable a small amount of contact surface between the knob 130 and the slot 210 to provide more free space by the non-contacting areas to enable cleaning of the apparatus. The top surface 510 of the knob 130 includes a rim 511 configured to surround the pressing spot 515 and connect to the four rounded corner portions 520 of the knob 130. The rim 511 may include several portions including a first flat portion 512, a curved portion 513, and a second flat portion 514 substantially perpendicular to the first flat portion 512. Though illustrated as separate, the first flat portion 512, curved portion 513, and second flat portion 514 are generally formed of one continuous piece of casted metal.

Embodiments described herein are configured to provide many openings between the knob 130 and the housing 120 to allow water, other liquids, and debris to pass through the knob 130 and housing 120 for cleaning and reprocessing of the quick coupling apparatus 100. On one wall 522 and an opposing wall (not illustrated) there are formed oval shaped wide openings 523 to take up most of the area of the wall 522 and opposing wall. Adjacent the wall 522 is another wall 524 including a pin slot 524a and a spring groove 524b that are separated by a spring support 530. The spring grooves 524b are positioned in the middle of the knob 130, equidistant from the wall 522 and opposing wall thereof. The wide openings 523 may provide spaces for water and other particles to flow. The pin slot 524a may guide the knob 130 into and out of the slot 210 around a pin (illustrated in FIG. 10). The pin is inserted through the pin hole 235 of the housing 120 and into the pin slot 524a. The pin will abut a pin contacting portion 530a of the spring support 530. When pressing the pressing spot 515 to insert or release an instrument, the pin slot 524a of the knob 130 will slide up and down around the pin. The pin is held in position by the tight fit into the housing 120 by the pin hole 235.

Because the walls 522 and 524 and opposing walls thereof are flat, the quick coupling apparatus 100 includes significant space between the walls and the cylindrical slot 210 for water, liquids, and other debris to pass through when cleaning. This ease of cleaning allows the cleaning process to be performed without removing the knob 130 from the housing 120, and without removing the quick coupling apparatus 100 from an adjoining handle.

An opposite wall (not illustrated) from the another wall 524 includes another spring groove 524b beneath another spring support 530. Above the spring support 530 on the opposite wall is an irrigation hole 535 to allow liquids and debris to pass through when cleaning or reprocessing. Inside the knob 130 are portions of a key hole structure 560 including a coupling surface 564 and large angled surface 564b configured to lock an instrument in place as described herein.

Figure 6:
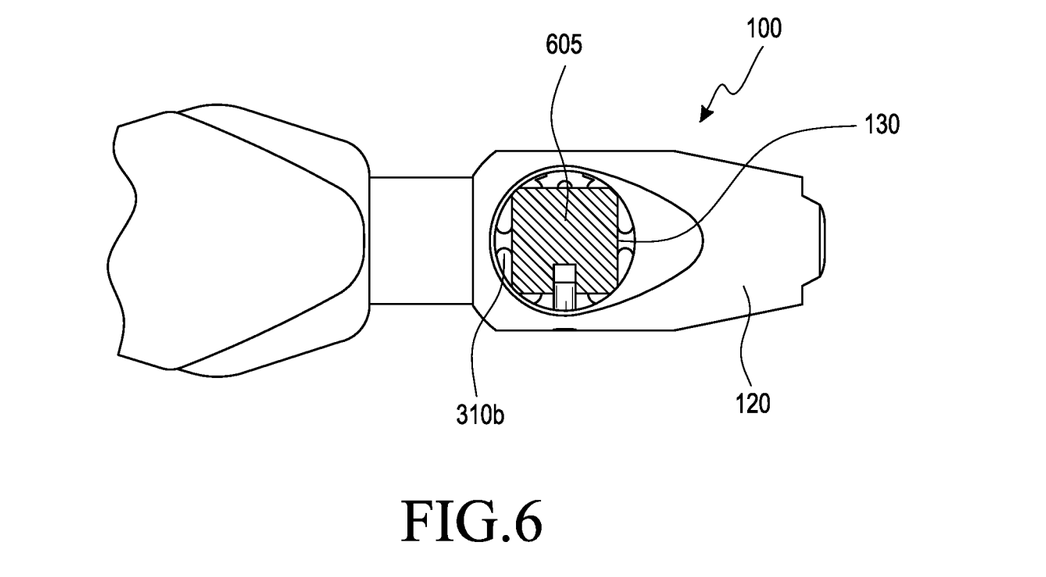
FIG. 6 illustrates a cross sectional view of the quick coupling apparatus having a housing with inserted knob in accordance with embodiments described herein.

FIG. 6 illustrates a cross-sectional view of the quick coupling apparatus 100 having a housing 120 with an inserted knob 130 having a rectangular top portion in accordance with embodiments described herein. The upper surface 605 of the knob 130 may have a generally rectangular shape or other polygonal shape that may be used for similar purpose as recognizable to one skilled in the art.

Figure 7:
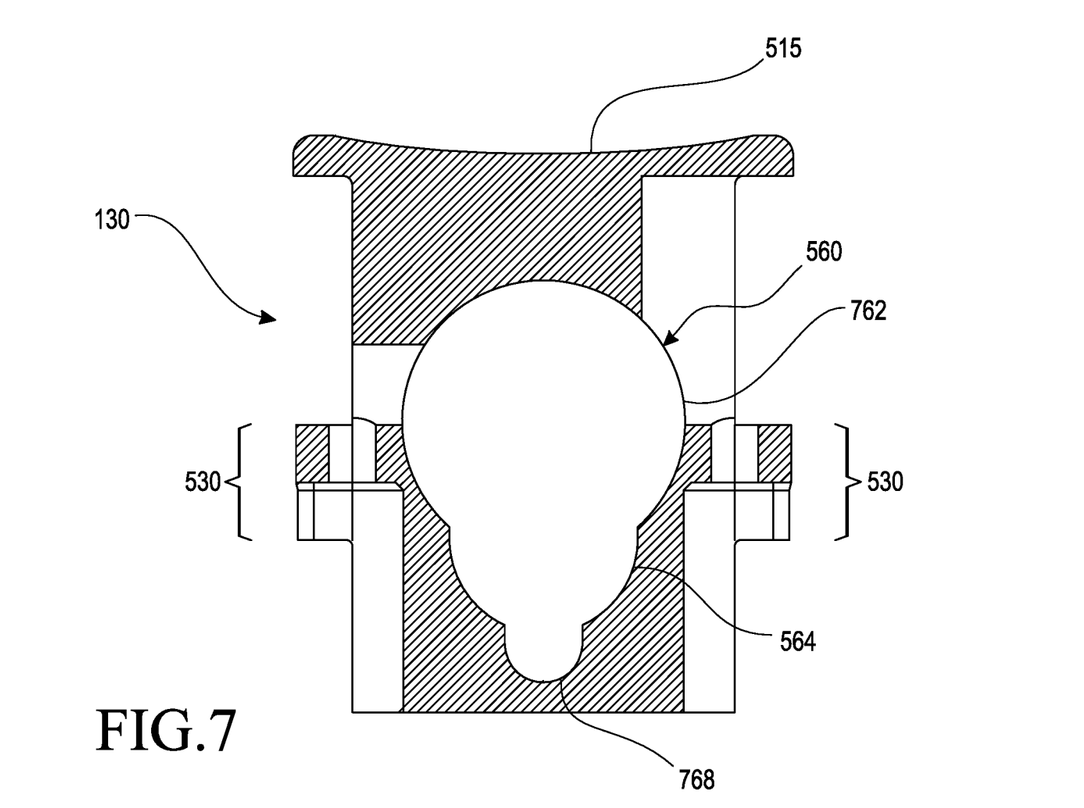
FIG. 7 illustrates a cross-sectional view of a knob in accordance with FIG. 5.

FIG. 7 illustrates a cross-sectional view of a knob 130 in accordance with FIG. 5. This view illustrates the key hole structure 560 through which an instrument bulb and neck (instrument 800 illustrated in FIG. 8) may be inserted. The key hole structure 560 includes three sections including an instrument receiving section 762, the coupling surface 564, and a milling groove 768. The milling groove 768 in the knob 130 prevents translating a forward movement of the instrument 800 into a decoupling movement of the knob 130. On either sides of the key hole structure 560 on opposing wall portions are disposed the spring supports 530. Springs (illustrated in FIG. 10) compress and release against the spring supports 530 to insert, couple, and release instruments from the quick coupling apparatus 100. Atop the knob 130 is the pressing spot 515. As illustrated, the pressing spot 515 may have a concave shape, indented inwards from the first flat portion 512 of the rim 511. The pressing spot 515 may have a depth on the order of 0.5 mm.

Figure 8:
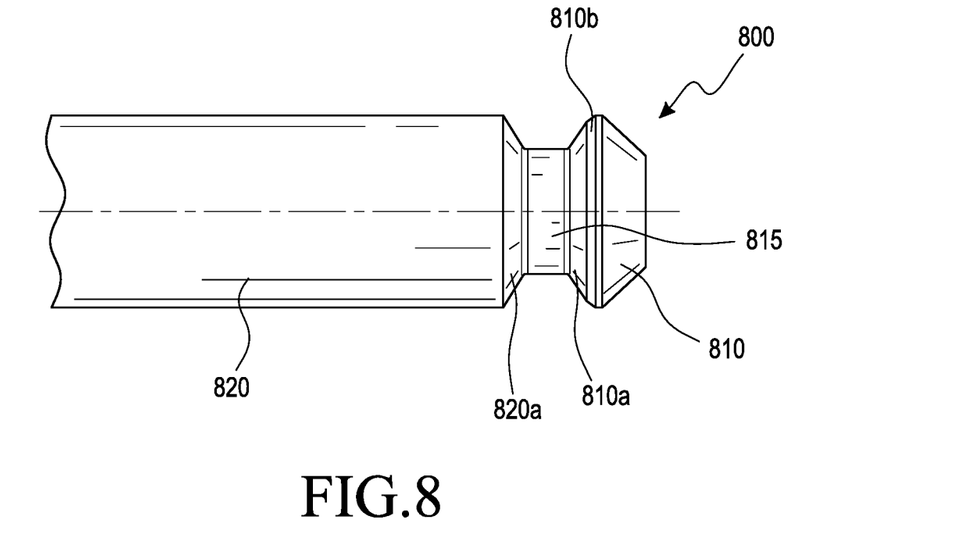
FIG. 8 illustrates an example of one end of a replaceable instrument that may be used with the quick coupling apparatus disclosed herein.

FIG. 8 illustrates an example of one end of a replaceable instrument that may be used with the quick coupling apparatus 100 disclosed herein. On one end of the instrument 800 is a bulb 810, a first angled surface 810a, an angled ridge 810b, a neck 815, a shaft portion 820, and a second angled surface 820a. The instrument 800 may be removably mounted into the key hole structure 560 of the knob 130. The instrument 800 may be one of a variety of replaceable chisels with varying heads. The instrument may also be one of a plurality of replaceable files, knives, mallots, bone curettes, elevators, or the like or other replaceable instruments that may be struck with a hammer or other blunt instrument as understood by one skilled in the art.

Figure 14:
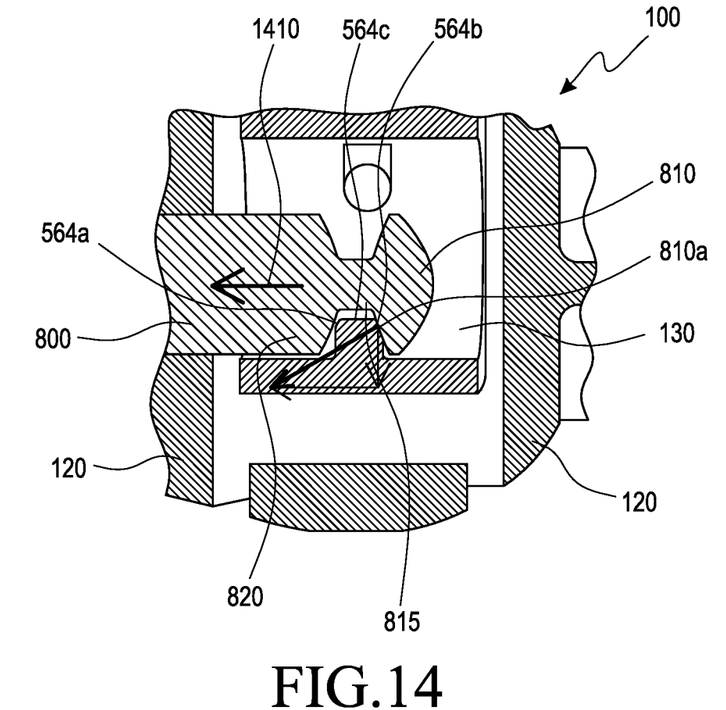
FIG. 14 is a cross-sectional view of the quick coupling apparatus in a direction of instrument insertion in accordance with embodiments described herein.

Referring to FIGS. 7 and 8, the key hole structure 560 is configured to receive an end of a replaceable instrument 800. The coupling surface 564 is configured to receive a neck 815 of the instrument 800. As illustrated in FIG. 14, the coupling surface 564 further includes a small angled surface 564a, a large angled surface 564b, and a flat surface 564c. When the bulb 810 of the replaceable instrument 800 is inserted through the channel 416 and through the second slot opening 414, the neck 815 of the instrument securely rests atop the coupling surface 564 of the knob 130. Locking of the instrument 800 into position and prevention of unwanted decoupling is done by coupling of the first angled surface 810a of the bulb 810 and large angled surface 564b of the coupling surface 564. When in position, the bulb 810 of the instrument 800 will be disposed on one side of the knob 130 and the shaft portion 820 will be on an opposite side with the neck 815 in the middle of the knob 130 resting on the coupling surface 564. According to embodiments described herein, coupling of an instrument 800 by the knob 130 may be in direction substantially perpendicular to a hitting direction on the distal end of the instrument handle 110. As a result of perpendicular coupling and a contact area formed between the coupling surface 564b and the first angled surface 810a, an instrument does 800 not get stuck in the quick coupling apparatus 100 due to sizing and does not release from coupling during free strikes to the distal end of the instrument handle 110.

Figure 15:
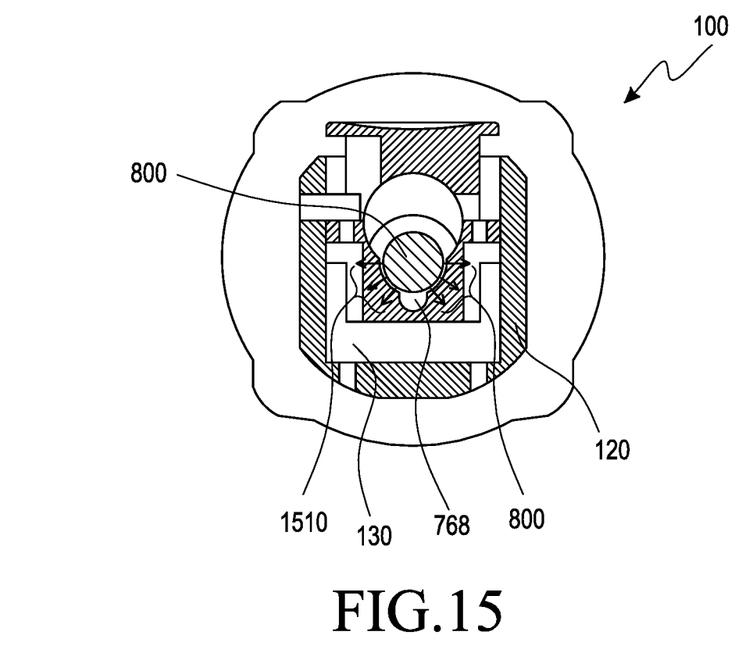
FIG. 15 illustrates a cross-sectional view of the quick coupling apparatus demonstrating impact forces upon the knob in accordance with embodiments disclosed herein.

Further prevention of decoupling is performed by the milling groove 768 The milling 768 groove prevents unwanted pure downward forces (as illustrated in FIG. 15) on the knob 130, when a chisel or other instrument is struck by a resistance free hammer blow, and prevents unintentional decoupling of the instrument.

Figure 9:
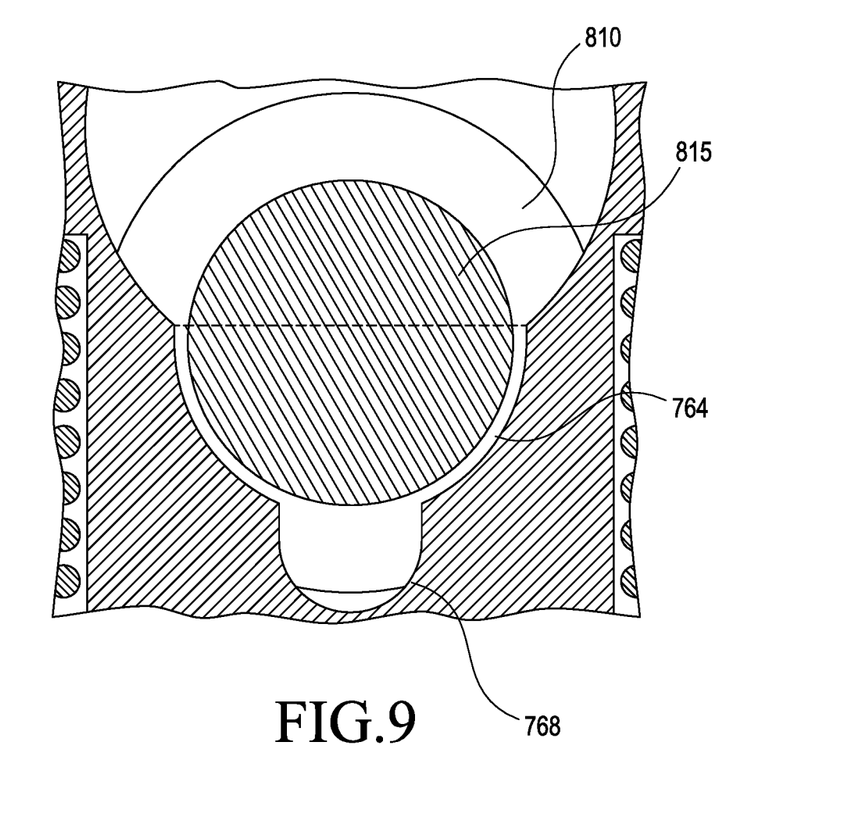
FIG. 9 illustrates a cross-sectional view of a bulb and neck in locked position in accordance with embodiments described herein.

FIG. 9 illustrates an enlarged cross-sectional view of a bulb 810 and neck 815 in locked position in accordance with embodiments described herein. In order to securely hold a neck 815 of an instrument 800 in position with the knob 130, the coupling surface 564 including the large angled surface 564b may have a circular surface configured to receive the bulb 810 including the first angled surface 810a on greater than one hundred eighty degrees of the circle caused by the coupling surface 564. This distance of greater than 180 degrees of the coupling surface 564 increases a contact area to offset a reduced contact area created by the milling groove 768. A combination of the enlarged contact area and milling groove prevents uncoupling and/or deformation of the instrument 800 during resistance free blows from a hammer or striking instrument to the distal end of the instrument handle 110.

Figures 10, 11, 12, 13:
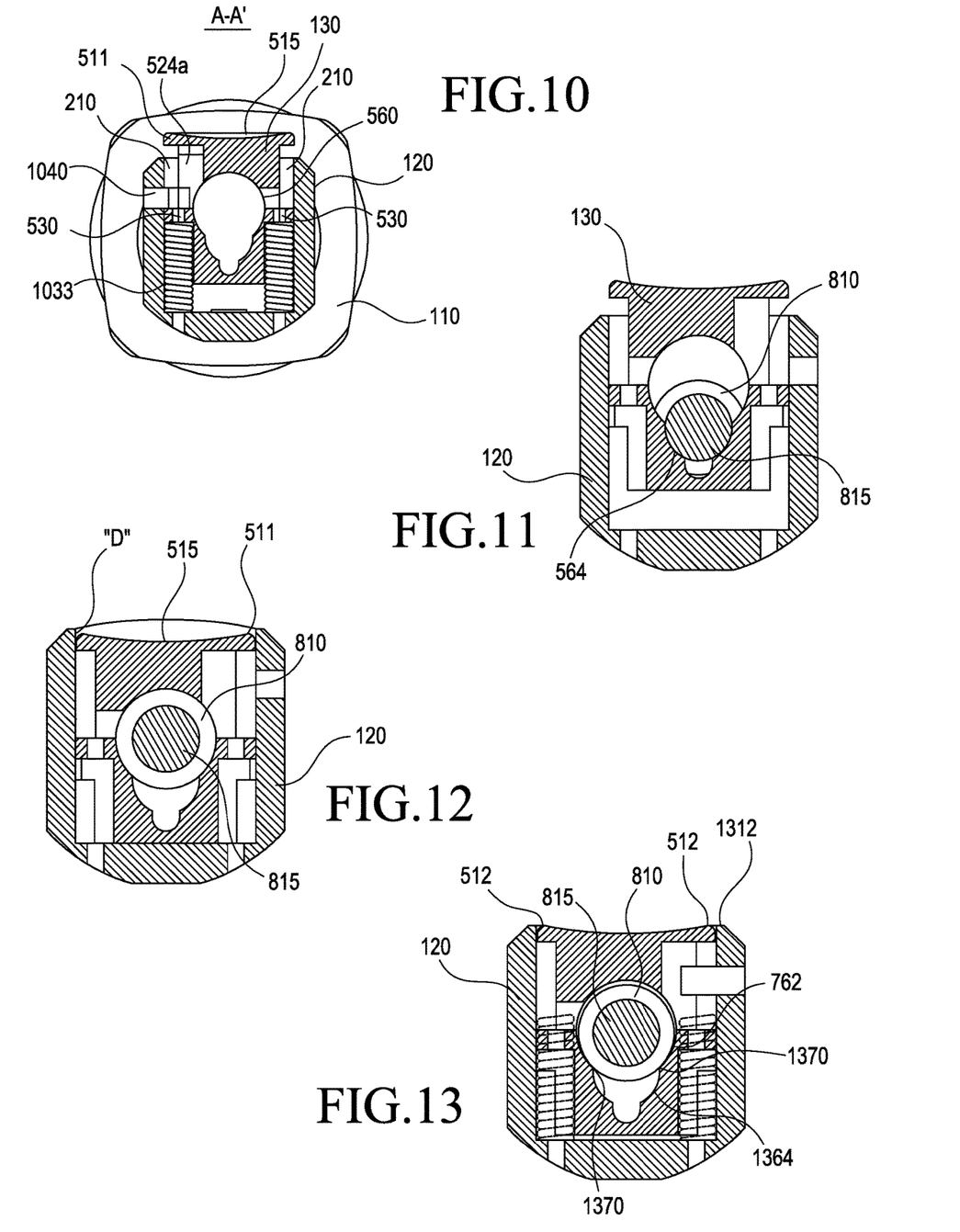
FIG. 10 illustrates a cross-sectional view of the quick coupling apparatus with a knob in locked position in accordance embodiments described herein.
FIG. 11 illustrates a cross-sectional view of the quick coupling apparatus with a knob coupling an instrument neck to a coupling surface in locked position in accordance with embodiments described herein.
FIG. 12 illustrates a cross-sectional view of the quick coupling apparatus with a knob and instrument bulb in open position in accordance with embodiments described herein.
FIG. 13 illustrates a cross-sectional view of the quick coupling apparatus with a knob and instrument bulb in partially-locked position in accordance with embodiments described herein.

FIG. 10 illustrates a cross-sectional view of the quick coupling apparatus 100 with a knob 130 in locked position without an instrument inserted in accordance embodiments described herein. Taken along cross sectional lines A-A' in FIG. 1, the knob 130 having the key hole structure 560 is illustrated in a locked position before an instrument has been inserted or after an instrument has been removed. When the quick coupling apparatus 100 is in locked position, the knob 130 protrudes from the housing 120. Illustrated in FIG. 10 are spaces of the slot 210 in which the knob 130 may move, spring supports 530, springs 1033, a pin 1040, and the pin slot 524a. Pressing the pressing spot 515 by a user allows the rim 511 of the knob 130 to slide back and forth within the slot 210. The pin 1040 may prevent unwanted rotation of the knob 130 when loading or unloading an instrument 800, or when there is no instrument 800 present. The spring supports 530 may be attached to or integrally formed with the knob 130 and interact with the springs 1033. When a user presses the pressing spot 515 to load or unload an instrument, one or two springs 1033 that have been installed in the quick coupling apparatus 100 will compress. When the pressing spot 515 is released, the spring or springs 1033 will expand, pushing the knob 130 to extend in a locked position protruding from the housing 120. A single spring in one spring groove 524b or two springs in two spring grooves 524b may be used to raise and lower the knob 130. Thus the knob 130 may be releasably positioned within the slot 210.

During initial assembly, once the springs 1033 are compressed, the pin 1040 is inserted into the pin hole 235 in the housing 120 to align with the pin slot 524a. The pin 1040 may include two diameters, a narrower portion to be inserted first followed by a wider portion to help hold the pin in place. The pin 1040 may be sized in this manner to make press fitting of the pin 1040 easier. Once the pin 1040 is inserted, the knob 130 may be released such that one of the spring supports 530 abuts the pin and prevents the knob 130 from being pulled out of the slot 210. The distance from the pin 1040 to the coupling surface has been predetermined such that when the spring support 530 abuts the pin 1040, the neck 815 of the instrument 800 is securely held within the housing 120. During manufacturing the pin 1040 is press fitted and welded to the housing 120.

FIG. 11 illustrates a cross-sectional view of the quick coupling apparatus 100 with a knob 130 coupling an instrument neck 815 to the coupling surface 564 in locked position in accordance with embodiments described herein. For simplicity, the pin and springs are not shown. FIG. 12 illustrates a cross-sectional view of the quick coupling apparatus 100 with a knob 130 and instrument neck in open position in accordance with embodiments described herein. FIG. 13 illustrates a cross-sectional view of the quick coupling apparatus 100 with a knob 130 and instrument bulb in partially-locked position in accordance with embodiments described herein.

A method of using the quick coupling apparatus 100 is described herein with reference to the accompanying figures. According to embodiments, to initially couple or release an instrument 800 that has been coupled within the quick coupling apparatus 100, a user may push the pressing spot 515 of the knob 130 from the locked position protruding outside the housing 120 as illustrated in FIG. 12 into the housing 120.

According to the design of the quick coupling apparatus 100, the entire top surface 505 of the knob 130 is pushed completely into the housing 120 in order for the instrument receiving section (762 illustrated in FIG. 7) of the knob 130 to align with the second slot opening 414 of the slot 210 and channel 416. To accomplish this, as illustrated in FIG. 12, the entire rim 511 and pressing spot 515 is pushed a distance D into the slot 210. A distance D may be, for example, 0.5 mm into the slot 210.

An instrument cannot be released or inserted, as illustrated in FIG. 13, if the first flat portion 512 of the rim 511 is only pushed to be flush with a flat portion 1312 of the housing 120. If this occurs, then corners 1370 between the coupling surface 564 and the instrument receiving section 762 will block or impede the removal or insertion of an instrument 800. Thus, embodiments described herein include the corners 1370 as a safety feature to prevent unintended release of an instrument 800. If the knob 130 is pressed against a flat surface that only presses the first flat portion 512 of the rim 511 flush with the housing 120, but not completely pushed into the slot 210, bulb 810 and first angled surface including the first angled surface 810a and the angled ridge 810b of the instrument 800 will be engaged by the corners 1370 and the instrument cannot be removed.

FIG. 14 is a cross-sectional view of the quick coupling apparatus 100 in a direction of instrument insertion in accordance with embodiments described herein. As illustrated in FIG. 14, the coupling surface 564 of the knob 130 may have a contour with a plurality of different shapes to accommodate an inserted instrument 800. The coupling surface in cross-section may include the small angled surface 564a, the large angled surface 564b, and the flat surface 564c that connects the small and large angled surfaces 564a and 564b. The small angled surface 564a may abut the opposing angled surface 820a of the instrument shaft 820. Locking of the instrument 800 into position is done by the first angled surface 810a of the bulb 810 and the large angled surface 564b of the coupling surface 564. The flat surface 564c may couple with an opposing flat surface of the inserted neck 815.

Due to the angle of the small angled surface 564a and the large angled surface 564b, when the strike cap of the handle 110 is acted upon, a forward movement 1410 in the direction of the arrow of the instrument 800 is translated onto the knob 130 into a forward movement and a radial movement.

FIG. 15 illustrates a cross-sectional view of the quick coupling apparatus 100 demonstrating impact forces upon the knob 130 in accordance with embodiments disclosed herein. When a strike cap 115 of an instrument handle 110 is acted upon, due to the reduced contact area on the knob 130 created by the milling groove 768, there is no pure downward movement of the instrument 800 within the quick coupling apparatus 100. FIG. 15 illustrates a plurality of force lines 1510 acting in a radial direction upon the coupling surface 564 including the large angled surface 564b. Because of the milling groove 768, there are no pure downward force lines in the force group 1510. Radial movement of the knob 130 is prevented by the housing 120. The remaining forces reflected on the instrument 800 do not exceed the combination of static friction between the coupling surface 564 and instrument 800, and the force of the springs 1033 pressing the knob 130 into a locked position. Thus the milling groove 768 assists in the stabilization of an instrument 800 mounted within the knob 130 of the quick coupling apparatus 100 and an instrument 800 does not decouple if there is a forward movement or force placed on the instrument.

According to embodiments described herein, the quick coupling apparatus 100 with handle offers an easy to use, easy to clean, safe and effective coupling mechanism for instruments. The quick coupling apparatus 100 with handle may be operated with one hand while a user's other hand inserts or releases an instrument. The design allows ease of cleaning, not requiring disassembly of the quick coupling apparatus from a handle, nor the knob 130 from the housing 120.

Although the various embodiments have been described in detail with particular reference to certain aspects thereof, it should be understood that the embodiments described herein are capable of other embodiments and its details are capable of modifications in various obvious respects. As is readily apparent to those skilled in the art, variations and modifications can be effected while remaining within the spirit and scope of the embodiments described herein. Accordingly, the foregoing disclosure, description, and figures are for illustrative purposes only and do not in any way limit the embodiments described herein, which is defined only by the claims.

The invention claimed is:

1. An apparatus configured to receive an instrument handle having a bulb with a first diameter and a cylindrical neck with a second diameter, where the second diameter is less than the first diameter, the apparatus comprising:
   a housing;
   a knob receivable in the housing, the knob having a key hole structure; and
   a slot in the housing configured to receive the knob, wherein:
      the knob is pressed into the slot to facilitate installation and removal of the instrument handle; and
      the key hole structure comprises an instrument receiving section with a third diameter, the instrument receiving section being configured to receive the bulb having the first diameter, and a coupling surface section with a circular inner edge configured to engage the cylindrical neck, the circular inner edge having a diameter which is less than the third diameter, wherein the coupling surface section comprises a milling groove.

2. The apparatus of claim 1, further comprising:
   at least one spring; and
   at least one spring support attached to the knob configured to compress and release the at least one spring.

3. The apparatus of claim 2, wherein the release of the at least one spring places the knob into a locked position.

4. The apparatus of claim 2, wherein the compression of the at least one spring places the knob into an open position to facilitate installation and removal of the instrument.

5. The apparatus of claim 1, wherein the slot is cylindrical.

6. The apparatus of claim 1, wherein the knob has four walls and an upper portion adjacent the four walls.

7. The apparatus of claim 5, wherein the knob has rounded edges to fit within the cylindrical slot.

8. The apparatus of claim 1, wherein the milling groove prevents unwanted decoupling of an inserted instrument.

9. The apparatus of claim 1, wherein the housing has a height and the knob is pressed into the slot below the height in order to install or remove the instrument.

10. The apparatus of claim 1, wherein the housing is configured to receive a replaceable instrument having a bulb, neck, and shaft.

11. The apparatus of claim 10, wherein the circular inner edge of the coupling surface section is configured to receive the cylindrical neck of the instrument on greater than one hundred eighty degrees of a circumference of the cylindrical neck.

12. The apparatus of claim 1, the apparatus being configured to receive the instrument handle, wherein the instrument handle has:
   the bulb with the first diameter;
   the cylindrical neck with the second diameter, where the second diameter is less than the first diameter; and
   a first angled surface connecting the bulb and the neck;
   wherein the key hole structure in the apparatus comprises an angled coupling surface configured to couple with the first angled surface.

13. The apparatus of claim 1, further comprising a plurality of drain holes formed in the housing.

14. The apparatus of claim 13, wherein the plurality of drain holes is formed on a side of the housing opposite to a mounting direction of the knob in the housing.

15. The apparatus of claim 1, wherein the knob includes a pressing spot having a concave surface.

16. The apparatus of claim 1, wherein the housing includes a pin hole configured to receive a pin in a direction perpendicular to a mounting direction of the knob in the housing.

17. The apparatus of claim 1, wherein the housing includes overhanging portions to prevent the instrument from rotating when coupled to the apparatus.

18. A method of using an apparatus according to claim 1 to lock an instrument handle into place, wherein the instrument handle has a bulb with a first diameter and a cylindrical neck with a second diameter, where the second diameter is less than the first diameter, the method comprising:
   pressing the knob into the slot to facilitate installation and removal of the instrument handle; and
   releasing the knob to lock the instrument handle into place with the key hole structure, wherein the coupling surface section of the key hole structure engages the cylindrical neck of the instrument handle.

19. The method of claim 18, wherein the instrument handle is received into the key hole structure of the housing, the key hole structure having an instrument receiving portion, a coupling surface section, and a milling groove.

20. The method of claim 19, comprising shifting the knob from a first position to a second position to lock the instrument handle into place, wherein in the first position the cylindrical neck of the instrument handle is substantially within the instrument receiving portion and in the second position the cylindrical neck of the instrument handle is substantially within the coupling surface section.

21. An apparatus configured to receive an instrument handle having a bulb with a first diameter and a cylindrical neck with a second diameter, where the second diameter is less than the first diameter, the apparatus comprising:
- a housing;
- a knob receivable in the housing, the knob having a key hole structure; and
- a slot in the housing configured to receive the knob, wherein:
    - the knob is pressed into the slot to facilitate installation and removal of the instrument handle; and
    - the key hole structure comprises at least two non-coaxial sections having different diameters, including a circular instrument receiving section configured to receive the bulb having the first diameter, and a coupling surface section with a circular inner edge configured to engage the cylindrical neck, wherein the coupling surface section comprises a milling groove.

* * * * *